US006649170B1

(12) United States Patent
Lindblad et al.

(10) Patent No.: US 6,649,170 B1
(45) Date of Patent: Nov. 18, 2003

(54) ADJUVANT COMBINATIONS FOR IMMUNIZATION COMPOSITION AND VACCINES

(75) Inventors: Erik B. Lindblad, Frederiksberg (DK); Martin J. Elhay, Hawthorn (AU); Peter Andersen, Bronshoj (DK); Lise Ostergaard Brandt, Copenhagen (DK)

(73) Assignee: Statens Serum Institut, Copenhagen (DK)

( * ) Notice: Subject to any disclaimer, the term of this patent is extended or adjusted under 35 U.S.C. 154(b) by 0 days.

(21) Appl. No.: 09/310,551

(22) Filed: May 12, 1999

(51) Int. Cl.$^7$ ................. A61K 39/04; A61K 39/02; A61K 45/00; A61K 47/00
(52) U.S. Cl. ................. 424/248.1; 424/184; 424/234.1; 424/278.1; 424/279.1; 424/280.1; 424/282.1; 424/283.1; 435/822; 530/300; 530/350
(58) Field of Search ................. 424/88, 92, 177, 424/184.1, 188.1, 182, 195, 197.1, 204, 278.1, 208.1, 275.1, 279.1, 280.1, 282.1, 283.1, 234.1, 257.1, 400, 418, 422, 450, 248.1; 435/236, 228, 239, 822; 514/25, 53, 54, 62, 723, 70.3, 960; 530/329, 300, 350

(56) References Cited

U.S. PATENT DOCUMENTS

| | | | | |
|---|---|---|---|---|
| 5,158,939 A | * | 10/1992 | Takayama et al. ............. | 514/53 |
| 5,554,372 A | * | 9/1996 | Hunter .................... | 424/280.1 |
| 5,679,354 A | * | 10/1997 | Morein et al. ........... | 424/278.1 |
| 5,762,943 A | * | 6/1998 | Dolovich et al. ......... | 424/275.1 |
| 5,773,011 A | | 6/1998 | Grubhofer | |
| 5,919,466 A | | 7/1999 | Grubhofer | |
| 5,951,988 A | | 9/1999 | Littel-van den Hurk | |

FOREIGN PATENT DOCUMENTS

| | | |
|---|---|---|
| DE | 19611235 C | 6/1997 |
| EP | 646378 A | 4/1995 |
| WO | WO95/01441 A | 1/1995 |

OTHER PUBLICATIONS

J. Rudbach et al, "Ribi Adjuvants: Chemistry, Biology and Utility in Vaccines for Human and Veterinary Medicine", The Theory and Practical Application of Adjuvants, Chapter 13, pp. 287–313, ed. D.E.S. Stewart–Tull, John Wiley & Sons, Ltd. (1995).

L. Brandt et al, "Protection Against Tuberculosis by ESAT–6 Vaccination", at The Fifth Elsinore Meeting on Infection–Immunity in Cellular Mechanisms and Molecules in Infection Immunity, Elsinore, Denmark (May 29–Jun. 2, 1998) (Abstract only).

G. K. Dzata et al, "Immunopotentiation of Cattle Vaccinated with a Soluble Brucella abortus antigen with Low LPS Content: an Analysis of Cellular and Humoral Immune Responses", Veterinary Microbiology, 29:15–26 (1991) Elsevier Science Publishers B.V., Amsterdam.

Lise Brandt et al, "ESAT–6 Subunit Vaccination Against Mycobacterium tuberculosis", Infection and Immunity, 68(2):791–795 (Feb., 2000).

K Lovgren–Bengtsson, "Chapter 6—Preparation and Use of Adjuvants", Methods in Microbiology, ed. S. HE Kaufmann and D. Kabelitz, vol. 25, pp. 471–502 (Academic Press, San Diego, 1998).

J. Cox et al, "Adjuvants—a Classification and Review of their Modes of Action", Vaccine, 15(3):248–256 (1997).

L. Brandt et al, "Key Epitopes on the ESAT–6 Antigen Recognized i Mice During the Recall of Protective Immunity to Mycobacterium tuberculosis", J. Immunol., 157:3527–3533 (1996).

E. Lindblad et al, "Adjuvant Modulation of Immune Responses to Tuberculosis Subunit Vaccines", Infection and Immunity, 65(2):623–629 (Feb. 1997).

P. Andersen, "Effective Vaccination of Mice Against Mycobacterium tuberculosis Infection with a Soluble Mixture of Secreted Mycobaterial Proteins", Infection and Immunity, 62(6):2536–2544 (Jun., 1994).

P. Andersen et al, "Proteins Released from Mycobacterium tuberculosis During Growth", Infection and Immunity, 59(6):1905–1910 (Jun., 1991).

P. Andersen et al, "T–Cell Proliferative Response to Antigens Secreted by Mycobacterium tuberculosis", Infection and Immunity, 59(4):1558–1563 (Apr., 1991).

J. Flynn et al, "An Essential Role for Interferon γ in Resistance to Mycobacterium tuberculosis Infection", J. Exp. Med., 178:2249–2254 (Dec., 1993).

A. Cooper et al, "Disseminated Tuberculosis in Interferon γ Gene–disrupted Mice", J. Exp. Med., 178:2243–2247 (Dec., 1993).

J. Grun et al, "Different T Helper Cell Subsets Elicited in Mice Utilizing Two Different Adjuvant Vehicles: The Role of Endogenous Interleuken 1 in Proliferative Responses", Cellular Immunology, 121:134–145 (1989).

* cited by examiner

Primary Examiner—Rodney P Swartz
(74) Attorney, Agent, or Firm—Howson and Howson

(57) ABSTRACT

A kit useful for immunization is described. The kit contains an antigenic substance from a Mycobacterium and an adjuvant combination of dimethyl dioctadecyl ammonium bromide and monophosphoryl lipid A.

10 Claims, No Drawings

ADJUVANT COMBINATIONS FOR IMMUNIZATION COMPOSITION AND VACCINES

The present invention relates to adjuvant combinations comprising two or more different adjuvants. In particular the invention relates to adjuvant compositions comprising the adjuvants in aqueous media for immunization and vaccines.

The invention also relates to vaccines and immunization combination kits comprising two or more adjuvants and an antigenic substance.

BACKGROUND OF THE INVENTION

Since the English doctor Edward Jenner in 1796 discovered that the infectious agency causing cowpox in cattle was able to produce immunity against smallpox in human beings without causing serious illness many efforts have been made in order to find other vaccines which can generate immunity against more or less severe diseases in animal and human beings without provoking the unpleasant, serious or fatal symptoms and reactions usually accompanying the ordinary diseases in question.

Thus, for example, tuberculosis in man has for many years been combated by vaccination with attenuated but living strains of *Mycobacterium bovis* (BCG vaccine). However, the efficacy of this procedure does not allways provide satisfactory resistance to human tuberculosis in every population.

Therefore, attempts have been made to isolate and use fragments or subfragments of strains of human *Mycobacterium tuberculosis* instead as immunogenic agent which when injected intradermally or subcutaneously in individuals would cause satisfactory immunity against infections with naturally occurring strains of human *Mycobacterium tuberculosis*. Thus, non-determined substances from culture filtrates as well as a few isolated molecules such as Ag85 and ESAT-6 of *Mycobacterium tuberculosis* have been shown to provide some degree of tuberculosis immunity.

In the future it would be desirable to have vaccines based on well-defined substances which would always create high immunity against tuberculosis and other diseases.

Unfortunately, many highly purified substances, e.g.. purified recombinant proteins, are not very immunogenic and do not generate an effective immune response protective against the real infectious disease. This fact has been recognized since the beginning of this century and it has been tried to counteract the low immunogenicity by combining the substance in question with immunogenic response potentiating agents, so-called adjuvants. A large number of such adjuvants and kind of adjuvants have been suggested but in general without any being ideal in all respects.

DISCLOSURE OF THE INVENTION

The present inventors have now discovered that two particular classes of adjuvants possess the capability to elicit a strong and long persisting immune response when administered in combination with an antigenic substance, even though this substance may have only poor immunogenicity per se.

Thus, the present invention relates to an adjuvant combination comprising a first adjuvant component which is a quaternary hydrocarbon ammonium halogenide of the formula $NR^1R^2R^3R^4$-hal, wherein $R^1$ and $R^2$ independently each is a short chain alkyl group containing 1 to 3 carbon atoms, $R^3$ and $R^4$ independently each is a hydrocarbon group containing from 12 to 20 carbon atoms, preferably from 14 to 18 carbon atoms and hal is a halogen atom, and a hydrophobic second adjuvant component In the formula $NR^1R^2R^3R^4$-hal the $R^1$ and $R^2$ groups may e.g. be methyl, ethyl, propyl and isopropyl, whereas $R^3$ and $R^4$ may be dodecyl, tridecyl, tetradecyl, pentadecyl, hexadecyl, heptadecyl, octadecyl nonadecyl and eicocyl groups. However, also other $C_{12}$–$C_{20}$ hydrocarbon groups are possible because even though the $R^3$ and $R^4$ groups usually and preferably are straight chain hydrocarbon groups they may in minor degree be branched having e.g. methyl and ethyl side chains. $R^3$ and $R^4$ may also have a minor degree of unsaturation, e.g. containing 1–3 double bonds each, but preferably they are saturated alkyl groups. $R^3$ and $R^4$ are preferably saturated alkyl groups containing from 14 to 18 carbon atoms.

The halogen atom "hal" is preferably bromine or chlorine because the other halogens, fluorine and iodine, may have undesirable biochemical, physiological and injurious effects, but for some experimental purposes, where such effects can be accepted, they may also be selected.

Preferably the hydrophobic second adjuvant component is selected from the group comprising triterpenoid saponins and derivatives thereof, lipopolysaccharides (LPS) and derivatives thereof, Staphylococcus antigen A, carbohydrate coupled phospholipids, monophosphoryl lipid A (MPL-A), mineral oil , Neem oil, taxol, the squalane and squalene series of adjuvants, block co-polymer adjuvants, pleuronic bloc polymer adjuvants, and lipoglycanes.

Examples of block co-polymer adjuvants are described by e.g. Todd C. V. et al., Systematic development of a block copolymer adjuvant for trivalent influenza virus vaccine, Dev Biol Stand 1998; 92:341–51.

Amongst the hydrophobic second adjuvant components, lipophilic adjuvants, such as monophosphoryl lipids (MPL), are prefered.

The monophosphoryl lipids (MPL) are e.g. obtainable from microbial lipopolysaccharide (LPS) and are usually prepared from bacterial polysaccharides even though other microbial sources like viruses, moulds, fungi, yeasts and algae may be the source of origin for the phosphoryl lipid of choice. Suitable bacterial polysaccharides are e.g. described in "The Theory and Practical Applications of adjuvants"[1], chapter thirteen, pp. 287–313, Ed. by D. E. S. Stewart-Tull, 1995, John Wiley Sons Ltd., in "Methods in Microbiology"[2], Vol. 25, pp. 471–502, Ed. Stefan A E Kaufmann and Dieter Kabelitz, 1998, Academic Press, San Diego, Calif., USA and London, UK, and in "Vaccine"[3], vol. 15, No. 3, pp. 248–256, 1997, Elsevier Science Ltd., GB.

Also, the monophosphoryl lipids derivable from the microbial polysaccharides and suitable for use in the adjuvant combinations of the present invention are described in more details in the above referrences. The preferred monophosphoryl lipid is monophosphoryl lipid A (MPL-A) which is described in 1) on pp. 289–292. in 2) on pp. 483–484, and in 3) on page 252, column 2. The most preferred MPL-A is designated 3-O-deacylated monophosphoryl lipid A. However, also other derivatives of the MPL-A's may be applicable.

The adjuvant combination of the present invention may preferably be in the form of:

a) an aqueous composition comprising the quaternary hydrocarbon ammonium halogenide of the formula $NR^1R^2R^3R^4$-hal, wherein $R^1$ and $R^2$ independently each is a short chain alkyl group containing 1 to 3 carbon atoms, $R^3$ and $R^4$ independently each is a medium chain length hydrocarbon group containing 12 to 20 carbon atoms and hal is a halogen atom, and b) an aqueous composition comprising the hydrophobic second adjuvant component.

The aqueous media in these aqueous compositions may be any suitable aqueous solvent. However, formation of useful possible micelle structures appears to be sensitive to anions, like phosphate and sulphate ions. Thus, it is preferred that the adjuvant compositions of the Inventions are formed in the absence or low levels of such ions.

The aqueous adjuvant compositions may be prepared by any suitable process or procedure, e.g. as described further on in the detailed part of this specification.

If expedient, the different adjuvant compositions may be combined into one single composition either as a stock composition or immediately before use.

The invention concerns also a kit for immunization, said kit comprising a first adjuvant component which is a quaternary hydrocarbon ammonium halogenide of the formula $NR^1R^2R^3R^4$-hal, wherein $R^1$ and $R^2$ independently each is a short chain alkyl group containing 1 to 3 carbon atoms, $R^3$ and $R^4$ independently each is a hydrocarbon group containing from 12 to 20 carbon atoms, preferably from 14 to 18 carbon atoms, and hal is a halogen atom, and a hydrophobic second adjuvant component and an antigenic substance.

Such kit may be presented in the form of individual containers or compartments containing the different adjuvants and the antigenic substance and any solvent necessary for effecting the immunization procedure as well as any necessary device for the performance thereof. If appropriate the adjuvants and the antigenic substance may also be combined and stocked in one single container. If the adjuvants and the antigenic substance each is contained in a separate container they may be mixed in any order before use. For some applications it may be advantageous, however, to mix the adjuvants and the antigenic substances in a particular order for obtaining optimum results.

In principle the antigenic substance may be any pure chemical species such as a protein or a fragment thereof or artificial mixtures prepared of such species. But it can also be any naturally occuring mixture of chemical species such as e.g. a cell homogenate or fractions thereof, a culture filtrate from microorganisms or cell tissues from multicellular organisms, e.g. higher animals.

Specifically the antigenic substance may be derived from a culture of metabolizing *Mycobacterium tuberculosis*, *Mycobacterium bovis* and other environmental Mycobacteria such as e.g. *Mycobacterium avium*. A particular interesting substance from the filtrate of such Mycobacteria is the ESAT-6 protein (Early Secretory Antigenic Target) which is a dominant target for cell mediated immunity in the early phase of tuberculosis in TB patients and in different animal models. It contains 95 amino acid residues and has a deduced molecular mass of approximately 10 kDa. Its immunogenicity per se is low, but in combination with the adjuvant combinations of the present invention it has turned out to be a potent candidate for provoking high and persisting immunity against tuberculosis as is demonstrated in the following detailed part of this specification.

ESAT-6 as well as many other antigens applicable in combination with the adjuvant combinations of the present invention, today can be produced artificially, e.g. synthetically or by genetic recombinant techniques.

In addition to provide immunity to diseases the adjuvant combinations of the present invention can also be used for producing antibodies against compounds which are poor immunogenic substances per se and such antibodies can be used for the detection and quantification of the compounds in question, e.g. in medicine and analytical chemistry.

Without being bound by theory it is believed that an adjuvant as DDA, which induces strong CMI (cell mediated immune) reponses, has the ability to form micelles in aqueous solutions. The lipid portion of this structure provides a matrix for the inclusion of other lipophilic compounds and the formation of composite micelles with increased adjuvant activity.

Preferred embodiments of the adjuvant combination and the immunization combination kit of the present invention are set forth in the dependent claims in the accompanying set of claims attached.

The invention will now be further described and illustrated by reference to embodiment examples of the invention and experimental examples forming the basis for the discovery of the present invention.

Materials and Methods

Animals

The studies were performed with 8 to 12 weeks old C57BL/6 (C57BL/6J, H-$2^b$) female mice, purchased from Bomholtegaard, Ry, Denmark.

Infected animals were housed in cages contained within a laminar flow safety enclosure.

Bacteria

*M. tuberculosis* H37Rv was grown at 37° C. on Löwenstein Jensen medium or in suspension in modified Sauton medium enriched with 0.5% sodium pyruvate and 0.5% glucose.

Adjuvants

DDA-Br (Eastman Kodak, Inc., Rochester, N.Y.) is mixed into sterile water to a concentration of 2.5 mg/ml and heated to 80° C. while stirring continuously on a magnetic stirring hotplate for 10 min and then cooled to room temperature before use.

MPL-A (MPL, Ribi Immunochem, Hamilton, Mont., USA) is mixed into sterile water to a concentration of 1 mg/ml containing 2 µl triethylamine. The mixture is heated in a 65–70° C. water bath for 30 seconds and then sonicated for 30 seconds. The heating and sonicating procedure is repeated twice. The solution is stored at 4° C. until use.

On the morning of immunization the antigen is mixed with saline and MPL-A (in the following abbreviated to MPL) is added. Then DDA-Br (in the following abbreviated to DDA) is added and the suspension is mixed on a vortex mixer.

Immunization

Mice were immunized three times with two weeks intervals subcutaneously (sc) in the back with the experimental vaccines which contained either 50 µg ST-CF/dose or 10–50 µg ESAT-6/dose emulsified in DDA (250 µg/dose, Eastman Kodak, Inc., Rochester, N.Y.) with or without 25 µg monophosphoryl lipid A (MPL, Ribi Immunochem, Hamilton, Mont., USA) in a volume of 0.2 ml.

A single dose of BCG Copenhagen 1331 ($5 \times 10^4$ cfu (colony forming units)) was injected subcutaneously at the base of the tail.

Experimental Infections

Intravenous (iv) infections were administered via the lateral tail vein with an inoculum of $5 \times 10^4$ *M. tuberculosis* (H37Rv) suspended in phosphate buffered saline (PBS) in a volume of 0.1 ml. The mice were sacrificed two weeks later.

Respiratory infections (ri) of the animals with *M.tuberculosis* (Erdman) were administered by the aerosol route with an inoculum of $5 \times 10^6$/ml. Six weeks later the mice were sacrificed.

Bacterial numbers in the liver, spleen or lung were determined by double serial 3 fold dilutions of individual whole organ homogenates on Middlebrook 7H11 medium. Organs from the BCG vaccinated animals were grown on medium supplemented with 2 $\mu$g 2-thiophene-carboxylic acid hydrazide (TCH). Colonies were counted after 3 weeks of incubation at 37° C. The protective efficacies are expressed as means of the bacterial counts in immunized mice after subtraction of the adjuvant control obtained from 5 animals/group.

Mycobacterial Antigens

Short-term culture filtrate (ST-CF) was produced as described previously {Andersen P., Askgaard D., Ljungqvist L., Bennedsen J., and Heron I., Proteins released from *Mycobacterium tuberculosis* during growth. Infect. Immun. 59: 1905–1910, 1991}. Briefly, *M tuberculosis* ($8\times10^6$ CFU/ml) were grown in modified Sauton medium without Tween 80 on an orbital shaker for 7 days. The culture supernatants were sterile filtered and concentrated on an Amicon YM3 membrane (Amicon, Danvers, Mass.)

Recombinant ESAT6 was prepared by Brandt et al. {Brandt L., Oettinger T., and Andersen P., Key epitopes on the ESAT-6 antigen recognized in mice during the recall of protective immunity to *Mycobacterium tuberculosis*. *J. Immunol.* 157:3527–3533, 1996} The LPS content in the preparations was measured by the LAL test to be below 0.3 ng/$\mu$g protein and this concentration had no influence on cellular activity. The protein was kept at $-80°$ C. until use.

Lymphocyte Cultures

Lymphocytes from spleens were obtained as described previously {Andersen P., Askgaard D., Ljungqvist L., Bentzon M. W., and Heron I., T-cell proliferative response to antigens secreted by *Mycobacterium tuberculosis*. *Infect. Immun.* 59: 1558–1563, 1991}. Blood lymphocytes were purified on density medium. Cells pooled from 3–5 mice in each experiment were cultured in microtiter wells (96 well, Nunc, Roskilde, Denmark) containing $2\times10^5$ cells in a volume of 200 $\mu$l RPMI 1640 supplemented with 2-mercaptoethanol, Penicillin-Streptomycin, glutamine and 5% (vol/vol) FCS (foetal calf serum). ST-CF and the preparations of ESAT-6 were used in various concentrations (2–20 mg/ml) in the cultures. Culture filtrate fractions were used at 5 mg/ml. Based on previous dose-response investigations, purified mycobacterial antigens and the peptides were all used at 5–10 mg/ml. Con A at a concentration of 1 mg/ml was used in all experiments as a positive control for cell viability. All preparations were tested in cell cultures and found to be non-toxic at the concentrations used in the present study. Supernatants were harvested from parallel cultures for the investigation of cytokines after 72 h of incubation.

IFN-$\gamma$ ELISA

Microtiter plates (96 well, maxisorb, Nunc) were coated with monoclonal Hamster anti-murine IFN-$\gamma$ (Genzyme, Cambridge, Mass.) in PBS at 4° C. Free bindings site were blocked with 1% (wt/vol) BSA/0.05% Tween 20. Culture supernatants were tested in triplicates and IFN-$\gamma$ was detected by biotin-labeled rat anti-murine monoclonal antibody (clone XMG1.2, Pharmingen, San Diego, Calif.). Recombinant IFN-$\gamma$ (Pharmingen) was used as a standard.

ELISPOT Technique

In this assay microtiter plates (96 well, maxisorb) were coated with 2.5 mg/ml of monoclonal hamster anti-murine IFN-$\gamma$ (Genzyme). Free binding sites were blocked with bovine serum albumin followed by washing with PBS/0.05% Tween 20. Analyses were always conducted on cells pooled from three mice. Cells were stimulated with optimal concentrations of antigen in modified RPMI 1640 for 18–22 h and subsequently cultured without antigen for 7 h directly in the ELISPOT plates. The cells were removed by washing and the site of cytokine secretion detected by biotin-labeled rat anti-murine IFN-$\gamma$ monoclonal antibody (clone XMG1.2, Pharmingen) and phosphatase-conjugated streptavidin (Jackson ImmunoResearch Lab., Inc., PA.). The enzyme reaction was developed with BCIP (Sigma). Blue spots were counted microscopically. The relationship between the number of cells per well and the number of spot was linear in concentrations $2\times10^5$–$6.2\times10^3$ cells/well. Wells with less than 10 spots were not used for calculations.

ESAT-6 Specific IgG ELISA

ELISA plates (NUNC Maxisorp, type 96F) were coated with ESATE-6 (0.1 $\mu$g/well) overnight at 4° C. Free binding sites were blocked by 1% bovine serum albumin-PBS. Individual mice sera from 5 mice/group were analyzed in three folds dilutions. IgG (P260, diluted 1/1000, DAKO) antibody was detected by peroxidase-conjugated rabbit anti-mouse reagent. Antibody titers are expressed as reciprocal end point titer.

Statistical Methods

Mean response to individual antigens were compared by the paired Student's t-test. The efficacies of different vaccination protocols have been compared by one-way analysis of variance of log 10 cfu (colony forming units).

EXAMPLE 1

ESAT-6 is Highly Recognized During Infection but not After Subunit Vaccination, i.e. ESAT-6 is a Low Immunogenic Molecule To study the immune response after vaccination with ESAT-6, C57BL/6 mice were vaccinated with an ESAT-6 subunit vaccine emulsified in DDA; an adjuvant which has been shown to induce an immune response of the Th1 type {Grun, J. L. and Maurer, P. H. Different T helper cell subsets elicited in mice utilizing two different adjuvant vehicles, *Cell Immunol.*, 121: 134–145, 1989; I Lindblad, E. B., Elhay, M. J. Silva, R., Appelberg, R and Andersen P., Adjuvant modulation of immune response to tuberculosis sub-unit vaccines, *Infect. Immun.*, 65(2): 623–629, 1997}. In parallel, groups of mice were immunized with experimental vaccines consisting of Short Term Culture Filtrate (ST-CF). All vaccines were given three times with a two week interval. One group of BCG vaccinated mice and one group of mice given a primary infection with *M. tuberculosis* were also included. The IFN-$\gamma$ contents in 72 h supernatents after stimulation of splenocytes from TB infected mice with ST-CF or ESAT-6 in vitro are shown in Table 1, column 2. Stimulation with ST-CF exhibited a powerful IFN-65 of 34,000 pg/ml followed up by a pronounced response to ESAT-6 (~19700 pg/ml).

The ability of the subunit vaccinations to generate an antigen specific immune response to the homologue preparation were investigated three weeks after the last booster injection by stimulating cells from the draining lymph nodes in vitro, Table 1, column 3. Of the immunized mice, the group of ST-CF vaccinated induced the strongest IFN-$\gamma$ release after stimulation with the homologue preparation (~19,150 pg/ml). In contrast, no ESAT-6 specific IFN-$\gamma$ response was detectable (<50 pg/ml).

TABLE 1

| | [a]IFN-$\gamma$ recall responses | |
| --- | --- | --- |
| [b]Antigen | [c]TB Infection | [d]Vaccination |
| Unstimulated | 1,405 ± 25 | 125 ± 25 |
| ST-CF | 34,317 ± 972 | 19,156 ± 987 |

TABLE 1-continued

$^a$IFN-γ recall responses

| $^b$Antigen | $^c$TB Infection | $^d$Vaccination |
|---|---|---|
| ESAT-6 | 19,668 ± 3281 | <50 |

$^a$Recall responses are expressed as mean IFN-γ contents representing the mean of triplicate values in pg/ml ± SEM in the supernatant monitored after 72 h. of in vitro stimulation.
$^b$Mice were vaccinated with BCG, ST-CF (50 μg/dose), or ESAT-6 (20 μg/dose) using DDA as adjuvant.
$^c$Spleen cells from mice infected i.v. with $5 \times 10^4$ cfu *M. tuberculosis* were isolated two weeks postinfection and a pool of cells from 5 mice was stimulated in vitro for 72 h whereafter the IFN-γ (pg/ml) contents in the supernatants were determined.
$^d$Lymph node cells were isolated three weeks after the last booster injection and a pool of cells from 5 mice was stimulated in vitro with the homologe protein. IFN-γ responses <50 were not detectable in this assay.

No Protection Obtained After Immunization with ESAT-6 in DDA

To study the protective efficacy of these experimental vaccines mice were left for three months after which the mice received either iv. or aerosol infection with live *M.tuberculosis*. The bacterial load in liver or lung were determined and the protective efficacy of these vaccines are expressed as the $\log_{10}$ reduction compared to the control mice, shown for two individual experiments in Table 2 (Expt. I and Expt. II). Vaccinations with either BCG or ST-CF/DDA evoked a significant protection of 0.73 $\log_{10}$ and 1.10 $\log_{10}$, respectively, compared to control mice, whereas no significant reduction of the bacterial load was detected after ESAT-6 vaccination, shown in Table 2, Expt. I. In experiment II the protective efficacy of BCG and ST-CF vaccination were confirmed. The ESAT-6/DDA vaccine did only evoke low levels of protection.

TABLE 2

$^a$Protection

| $^b$Vaccination | $^c$Expt. I | $^d$Expt. II |
|---|---|---|
| BCG | 0.73 ± 0.06 (p = 0.008) | 0.98 ± 0.22 (p = 0.008) |
| ST-CF | 1.10 ± 0.09 (p = 0.008) | 0.81 ± 0.17 (p = 0.006) |

TABLE 2-continued

$^a$Protection

| $^b$Vaccination | $^c$Expt. I | $^d$Expt. II |
|---|---|---|
| ESAT-6 | 0.11 ± 0.10 | 0.25 ± 0.09 (p = 0.009) |

$^a$The protective efficacies of vaccines are expressed as the $\log_{10}$ reduction of the bacterial load. Data expressed are means based on duplicate analysis for each group (n = 5). P values have been given for bacterial load that are significantly different from numbers found for unimmunized control mice determined by student's t-test.
$^b$Mice were BCG vaccinated or immunized s.c. with experimental vaccines emulsified in DDA.
$^c$Protection obtained in the liver of C57BL/6 mice after TB infection given iv.
$^d$Protection obtained in the lung after aerosol TB infection.

EXAMPLE 2

DDA Combined with MPL Promotes an Efficient Response to ESAT-6

It is a general accepted fact that adjuvants have some selectivity for the induction of a certain class of immune response. Since the importance of a Th1 cytokine release based on IFN-γ production has been shown to be essential in the resistance to TB {Flynn J. L., Chan J., Triebold K. J., Dalton D. K., Stewart T. A., and Bloom B. R., An essential role for interferon gamma in resistance to *Mycobacterium tuberculosis* infection, j.Exp.Med., 178:2249–2254, 1993; and Cooper A. M., Dalton D. K., Stewart T. A., Griffen J. P., Russel D. G., and Orme I., M. Disseminated tuberculosis in interferon gamma gene-disrupted mice, *J.Exp.Med.*, 178:2243–2247,1993}, MPL was added to the ESAT-6/DDA preparation in the attempt to investigate the potential of this vaccine. Mice were immunized three times and one week after the $3^{rd}$ vaccination the ESAT-6 specific immune responses of blood cells were investigated. Only minimal T cell recognition of ESAT-6 could be detected from mice which received ESAT-6 mixed with DDA. In contrast, immunization with ESAT-6 emulsified in DDA+MPL generated a very potent IFN-γ response and very high frequencis of cells secreting IFN-γ (1:470), measured by the sensitive ELISPOT technique, table 3.

The development of the ESAT-6 specific antibody response was investigated in mice 7 weeks after the first vaccination shown in table 3. High titers of ESAT-6 specific IgG are present in the sera from mice vaccinated with ESAT-6/DDA+MPL compared with the amounts found in sera after ESAT-6/DDA vaccination.

TABLE 3

| | ESAT-6 specific recall response | | | | |
|---|---|---|---|---|---|
| | Expt. I | | | Expt. II | |
| $^a$Vaccine | $^b$IFN-γ | $^c$Frequency | $^d$ESAT-6 specific IgG | $^c$Frequency | $^d$ESAT-6 specific IgG |
| DDA | <50 | <1:20,000 | <3 | <1:20,000 | <3 |
| DDA + MPL | <50 | <1:20,000 | <3 | <1:20,000 | <3 |
| ESAT-6 + DDA | <50 | 1:14,800 | 32,768 | 1:8,700 | 65,530 |
| ESAT-6 + DDA/MPL | 12,235 ± 553 | 1:470 | 262,144 | 1:440 | 524,288 |

$^a$Mice were vaccinated with adjuvant or ESAT-6 subunit vaccines (10 μg/dose) three times with a 2 week interval.
$^b$Means of the IFN-γ responses in pg/ml measured in 72 h. supernatant of blood cell cultures one week after the last booster injection
$^c$Frequencies of IFN-γ producing lymphocytes were estimated by ELISPOT analysis of blood cells established from immunized mice one week after the last booster injection. Frequencies were estimated from a pool of 5 mice. The results are expressed as mean of duplicate values and the difference between duplicate cultures are <12% of the mean. Frequencies lower than 1:20,000 were not detectable in this assay.
$^d$5 weeks after the primary vaccination, sera were determined by ELISA as described in Materials and Methods. The data listed are the end-point titers of a pool of sera from 6. The results listed are mean of dublicate values and the difference between dublicate wells are <11%.

EXAMPLE 3

Protective Efficacy of the ESAT-6 Vaccine

In order to measure the efficacies of the ESAT-6/DDA+MPL vaccine the mice were challenged with an aerosol administration of *M.tuberculosis* (Erdman) 6–8 weeks after the last ESAT-6 immunization and 6 weeks post infection the spleen and lung were harvested for determination of the bacterial load. As shown in table 4 the protection obtained from ESAT-6/DDA+MPL vaccination was similar to that induced by BCG vaccination with no significant difference in any of the two experiments described. In contrast, the ESAT6/DDA vaccine did not protect significantly compared to the unvaccinated control, neither in the spleen nor in the lung.

TABLE 4

| Experiment | [a]Vaccine | [b]$Log_{10}$ resistance Spleen | Lung |
|---|---|---|---|
| I | DDA | <0.05 | <0.05 |
|  | DDA + MPL | <0.05 | <0.05 |
|  | ESAT-6/DDA | [c]0.28 (±0.14) | 0.18 (±0.12) |
|  | ESAT-6/DDA + MPL | [c]0.58 (±0.10) | [c]0.41 (±0.05) |
|  | BCG | [c]0.53 (±0.19) | [c]0.77 (±0.06) |
| II | DDA + MPL | <0.05 | <0.05 |
|  | ESAT-6/DDA + MPL | [c]0.89 (±0.32) | [c]0.50 (±0.09) |
|  | BCG | [c]0.94 (±0.24) | [c]0.46 (±0.09) |

[a]Mice were vaccinated s.c. with ESAT-6 subunit vaccines (10 μg/dose) three times with 2 weeks intervals or BCG vaccinated (4 × $10^5$ cfu).
[b]The bacterial load is expressed as the $log_{10}$ reduction measured in the spleen and lung 6 weeks after aerosol challenge.
[c]Protective efficacies which are significantly different from control mice, determined by Student's t-test.

EXAMPLE 4

Enhancement of the Protective Efficacy of Adding MPL to Vaccines Based on Highly Immunogenic Molecules Vaccination of C57BL mice with ST-CF emulsified in DDA has been shown to induce a protection at levels comparable to BCG {Andersen P., Effective vaccination of mice of mice against *Myccobacterium tuberculosis* infection with a soluble mixture of secreted mycobacterial proteins., *Infect Immun.* 62: 2536–2544, 1994}.

To analyse the protective capacity of vaccines consisting of ST-CF in DDA+MPL we immunized C57BL mice with ST-CF mixed in this vaccine. None of the adjuvants alone raised a protective immune response (data not shown), neither did ST-CF emulsified in MPL alone, Table 5. After adding MPL to the ST-CF/DDA vaccine the IFN-γ response of this highly immunogenic antigen preparation was enhanced a 10 fold, and the protective efficacy was also significantly enhanced compared to a similar vaccine mixed with DDA alone. This demonstrate a lack of efficacy using MPL on its own but at the same time an efficient coadjuvant to DDA promoting an efficient protective immune response.

TABLE 5

| [a]Vaccine | [b]IFN-γ (pg/ml) | [c]$Log_{10}$ resistance |
|---|---|---|
| MPL + ST-CF | 1003 | 0.10 ± 0.08 |
| DDA + ST-CF | 458 | 0.69 ± 0.10 |
| MPL + DDA + ST-CF | 4936 | 0.93 ± 0.11 |
| BCG | 588 | 1.29 ± 0.09 |

[a]Mice were vaccinated s.c. with experimental subunit vaccines (100 μg/dose) twice with 2 weeks intervals or BCG vaccinated (4 × $10^5$ cfu).
[b]Splenocytes were stimulated in vitro with ST-CF (4 μg/ml) and the IFN-γ contents were measured in 72 h. supernatants. The results are expressed as mean of dublicate values and the difference between dublicate cultures are <6% of the mean. IFN-γ responses <50 were not detectable in this assay.
[c]The bacterial load after i.v. challenge expressed as the $log_{10}$ reduction measured in the spleen compared to unvaccinnated control.

Concluding Remarks

The selection of adjuvants having no or low levels of undesired side effects are quite limited. $Al(OH)_3$, which is known to prime mainly a Th2 type immune response, is the only adjuvant which is licensed for human use today. DDA and MPL are both mild adjuvants and may therefore be potential candidates for human use. As shown in the above studies using ESAT-6 as a model, antigen mixed with a combination of DDA+MPL clearly demonstrate that MPL amplify some of the crucial events in the protective immunological cascade after vaccination. These findings imply that a vaccine based on even low immunogenic molecules used in combination with DDA+MPL can be a highly efficient way of triggering the right type of immune response.

The use of this new combination of adjuvants has been demonstrated along with TB antigens, but the use of this combination may be of great value for other antigens found outside the TB field.

We claim:

1. An immunization combination kit comprising:
   (a) an antigenic substance from a culture of metabolizing *Mycobacterium tuberculosis;* and
   (b) an adjuvant combination consisting of dimethyl dioctadecyl ammonium bromide (DDA-Br) and monophosphoryl lipid A (MPL-A) in a ratio of from 30:1 to 4:1 by weight.

2. The immunization kit of claim 1, wherein the antigenic substance is Early Secretory Antigenic Target (ESAT)-6.

3. The immunization combination kit according to claim 1, which comprises DDA-Br and MPL-A in a ratio of from 20:1 to 5:1 by weight.

4. The immunization combination kit according to claim 1, which comprises DDA-Br and MPL-A in a ratio of about 10:1 by weight.

5. An immunization combination kit comprising:
   (a) a Mycobacterium antigen; and
   (b) an adjuvant combination consisting of dimethyl dioctadecyl ammonium bromide (DDA-Br) and monophosphoryl lipid A (MPL-A) in a ratio of from 30:1 to 4:1 by weight.

6. The immunization combination kit according to claim 5, which comprises DDA-Br and MPL-A in a ratio of from 20:1 to 5:1 by weight.

7. The immunization combination kit according to claim 5, which comprises DDA-Br and MPL-A in a ratio of about 10:1 by weight.

8. An improved composition for immunization comprising a Mycobacterium antigen,
   wherein said improvement consists of an adjuvanting amount of an adjuvant combination consisting of dimethyl dioctadecyl ammonium bromide (DDA-Br) and monophosphoryl lipid A (MPL-A) in a ratio of from 30:1 to 4:1 by weight.

9. The improved composition according to claim 8, wherein the ratio is from 20:1 to 5:1.

10. The improved composition according to claim 8, wherein the ratio is about 10:1.

* * * * *